United States Patent [19]
McFarland

[11] 3,948,911
[45] Apr. 6, 1976

[54] SUBSTITUTED QUINOXALINE-2-CARBOXAMIDE 1,4-DIOXIDES

[75] Inventor: James W. McFarland, Lyme, Conn.

[73] Assignee: Pfizer Inc., New York, N.Y.

[22] Filed: Nov. 19, 1974

[21] Appl. No.: 525,183

[52] U.S. Cl. ............... 260/250 QN; 260/243 B; 260/247.5 DP; 260/268 C; 260/307 G; 260/349; 424/250; 424/248; 424/246
[51] Int. Cl.$^2$ ............... C07D 241/44
[58] Field of Search ............... 260/250 QN

[56] References Cited
UNITED STATES PATENTS

| | | | |
|---|---|---|---|
| 3,660,391 | 5/1972 | Ley | 260/250 |
| 3,663,697 | 5/1972 | Conover | 260/250 |
| 3,682,906 | 8/1972 | Seng | 260/250 |
| 3,801,711 | 4/1974 | Seng | 260/250 |
| 3,803,145 | 4/1974 | Abushanab | 260/250 |

Primary Examiner—Richard J. Gallagher
Assistant Examiner—Mark L. Berch
Attorney, Agent, or Firm—Connolly and Hutz

[57] ABSTRACT

Compounds of the formula

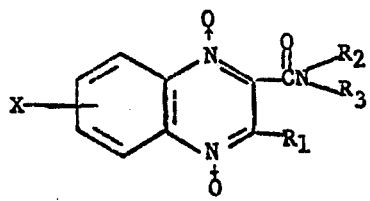

wherein X is a 6- or 7-position substituent selected from the group consisting of formyl, acetyl, hydroxymethyl, 1-hydroxyethyl and

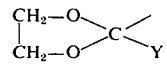

wherein Y is selected from the group consisting of hydrogen and methyl; $R_1$ is hydrogen or methyl; $R_2$, when taken separately, is hydrogen or alkyl having 1 to 4 carbon atoms; $R_3$, when taken separately, is hydrogen, alkyl having 1 to 4 carbon atoms, $-(CH_2)_nOH$, $-(CH_2)_nOCH_3$, $-(CH_2)_nNH_2$,

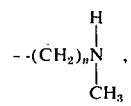

or

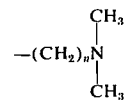

wherein $n$ is 2 or 3 and $R_2$ and $R_3$, when taken together with the nitrogen atom to which they are attached, form a member selected from the group consisting of pyrrolo, pyrrolidino, piperidino, morpholino, thiomorpholino, piperazino, N-(lower alkyl)-piperazino, N-hydroxy(lower alkyl)piperazino, N-(lower alkanoyl)piperazino and N-carbo(lower alkoxy)piperazino and the pharmaceutically acceptable acid addition salts of those compounds wherein $R_2$ has an ω-aminoalkyl moiety; methods for their preparation; and their use as antibacterial agents and as agents for promoting growth and improving feed efficiency of animals.

11 Claims, No Drawings

SUBSTITUTED QUINOXALINE-2-CARBOXAMIDE 1,4-DIOXIDES

BACKGROUND OF THE INVENTION

This invention relates to substituted quinoxaline-2-carboxamide-1,4-dioxides which are useful antibacterial agents for the control of various pathogenic microorganisms and as animal growth promotants.

Various analogs of the compounds of the present invention are known in the prior art to be useful for such purposes. Typical examples of these prior art analogs are disclosed in U.S. Pat. Nos. 3,660,391 and 3,682,906. Whereas these prior art analogs do have useful activity for the stated purposes, it has been found that they display certain toxic side effects when used, for example, in animal feeds. Unexpectedly, it has been found that the compounds of the present invention display a marked unexpected reduction in these side effects and may, therefore, be used with a higher degree of safety or in larger amounts for more rapid control of various pathogenic microorganisms and/or as animal growth promotants.

SUMMARY OF THE INVENTION

It has been found that a series of substituted quinoxaline-2-carboxamide-1,4-dioxides are valuable antibacterial agents. These compounds have the formula

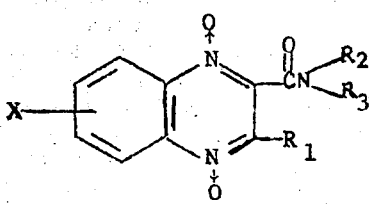

wherein X is a 6- or 7-position substituent selected from the group consisting of formyl, acetyl, hydroxymethyl, 1-hydroxyethyl and

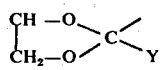

wherein Y is selected from the group consisting of hydrogen and methyl; $R_1$ is hydrogen or methyl; $R_2$, when taken separately, is hydrogen or alkyl having 1 to 4 carbon atoms; $R_3$, when taken separately, is hydrogen, alkyl having 1 to 4 carbon atoms, $-(CH_2)_nOH$, $-(CH_2)_nOCH_3$, $-(CH_2)_nNH_2$,

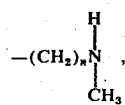

or

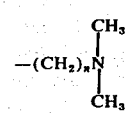

wherein $n$ is 2 or 3 and $R_2$ and $R_3$, when taken together with the nitrogen atom to which they are attached, form a member selected from the group consisting of pyrrolo, pyrrolidino, piperidino, morpholino, thiomorpholino, piperazino, N-(lower alkyl)piperazino, N-hydroxy(lower alkyl)piperazino, N-(lower alkanoyl)piperazino and N-carbo(lower alkoxy)piperazino and the pharmaceutically acceptable acid addition salts of those compounds wherein $R_2$ has an ω-aminoalkyl moiety.

By the terms lower alkyl, lower alkoxy, lower alkanoyloxy and lower alkanoyl are meant those alkyl, alkoxy, alkanoyloxy and alkanoyl groups which contain from 1 to 4 carbon atoms, i.e., those which are conveniently prepared from readily available starting materials.

The compounds of this invention are effective antibacterials both in vitro and in vivo. Additionally, the herein described compounds are effective animal growth promotants, particularly for swine and poultry.

Especially preferred compounds of the present invention include those of the aforesaid formula wherein X is acetyl. Among these an especially preferred group includes those wherein $R_1$ is methyl, and each of $R_2$ and $R_3$ is hydrogen or methyl. Another preferred group of compounds are those wherein X is hydroxymethyl, $R_1$ is methyl and each of $R_2$ and $R_3$ is hydrogen or methyl. Still another preferred group is that wherein X is 1-hydroxyethyl, $R_1$ is methyl and each of $R_2$ and $R_3$ is hydrogen or methyl.

An especially preferred group of compounds are those wherein X is

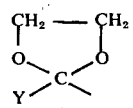

$R_1$ is methyl and each of $R_2$ and $R_3$ is hydrogen or methyl.

The compounds of this invention may be prepared via a variety of methods. Method A involves reacting the appropriate benzofuroxan with the desired amino containing reactant, e.g., $HNR_2R_3$, and diketene in at least equimolar proportions. Method B comprises reacting a benzofuroxan with an appropriate β-ketoamide, e.g. $R_1$—CO—$CH_2$—CO—$NR_2R_3$ in the presence of a base catalyst. Method C involves reacting an ester of an appropriate 2-quinoxaline-carboxylic acid 1,4-dioxide with the appropriate amino containing reactant, $HNR_2R$. In method D, the appropriate benzofuroxan reactant is allowed to react with an aceto ester with the appropriate amino containing reactant, $HNR_2R_3$.

Compounds wherein X is

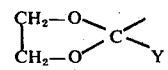

are prepared from the formyl or acetyl derivatives by reaction with ethylene glycol in an organic solvent in the presence of an acid catalyst.

DETAILED DESCRIPTION OF THE INVENTION

The novel compounds of this invention can be prepared by several methods. The first method (method A) is the preferred one since it utilizes readily available materials, is simple and convenient and productive of good yields of the desired product. This reaction, in its broadest sense, comprises reacting the appropriate benzofuroxan with the desired amino containing reactant, e.g., $HNR_2R_3$, and diketene (ketene dimer) in at least equimolar proportions. In general, an excess of the amine reactant is used since the reaction with the benzofuroxan is most readily conducted in the presence of a base catalyst. For the instant process, an excess of the amine reactant, which is frequently the most readily available and most economical of the reactants used, conveniently serves as catalyst. The amount of excess amine used is not critical. It is, however, advantageous to use up to a 50 percent molar excess of the amine based on the diketene or benzofuroxan used, in order to insure complete reaction plus sufficient base to serve as catalyst. The use of a larger excess of amine appears to serve no useful purpose. Alternatively, a separate base which does not enter into the reaction except to serve as catalyst, can be used in place of excess of the amine reactant. The separate base can be a tertiary amine, an alkali metal alkoxide, an alkali metal or alkaline earth metal hydroxide, or a metal hydride. Representative of such bases are 1,5-diaza-bicyclo [4.3.0]-5-nonene, triethylamine, 1,2-dimethyl-1,4,5,6-tetrahydropyrimidine, sodium methoxide, potassium ethoxide, alcoholic potassium hydroxide and sodium hydride. In such instances, as noted above, the amine reactant is used in approximately equimolar proportions to the diketene or benzofuroxan. The separate base is normally used up to one-half mole per mole of the diketene or benzofuroxan. Larger amounts of added base are of no apparent advantage. It can be added to the reaction mixture before, with or after the amine reactant, or with the benzofuroxan reactant.

The reaction is usually conducted in an appropriate solvent system, that is a reaction-inert solvent or mixture of solvents, which serves to dissolve at least the reactants and which does not enter into adverse reactions with the reactants or products. Suitable solvents are ethers such as diethylether, diisopropylether, dioxane, tetrahydrofuran, dimethylethers of ethyleneglycol and diethyleneglycol, alcohols especially the lower molecular weight alcohols having up to four carbon atoms, N,N-dimethylformamide, benzene, toluene, xylene, acetonitrile, halogenated hydrocarbons such as chloroform, methylene chloride and mixtures of these solvents.

The reaction is normally conducted over the temperature range of from about 0°C. to about 100°C. Higher temperatures can be used but appear to offer no advantage and may in certain cases cause decomposition. The reaction period, as expected, depends upon the reactants and the temperature used. For a given set of reactants, the higher the reaction temperature, the shorter the reaction period; the lower the reaction temperature, the longer the reaction period.

The order of addition of reactants is not critical to the success of this process. The reaction can be conducted by simultaneous or stepwise addition of the various reactants including the excess amine or separate base as catalyst.

From a practical standpoint in order to achieve maximum yield of the desired 2-quinoxalinecarboxamide-1,4-di-oxide, it is advantageous to react the diketene and amine containing reactant together in an appropriate solvent system for a brief period before adding the benzofuroxan. A preferred method comprises adding a solution of the desired amine in a reaction-inert solvent to at least an equimolar solution of diketene in the same or other reaction-inert solvent which is miscible with the amine solvent at a temperature of from about 0°C. to about 30°C. The mixture is then treated immediately with the catalyst and benzofuroxan reactant by dissolving this last reactant into the amine-diketene reaction mixture. The temperature of this phase of the reaction is not critical but can range up to about 100°C. In most instances, the temperature of this phase is kept below about 60°C. and is frequently run at room temperature for periods of up to twenty-four hours. In most instances, the reaction mixture is allowed to stand at room temperature for several hours, e.g., overnight.

The reaction products frequently separate from the reaction mixture as solids, often crystalline solids, which are recovered by filtration or centrifugation and recrystallized, if desired, for further purification. The products, if not solids which separate upon standing, are recovered by precipitation from the reaction mixture by addition of a suitable solvent, more accurately, a non-solvent for the product. The precipitated product is then recovered as above. Alternatively, the product is recovered by evaporation of the solvent.

A second method (method B) broadly comprises reaction of a benzofuroxan with an appropriate N-substituted β-ketoamide, such as those of the formula

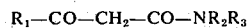

$$R_1-CO-CH_2-CO-NR_2R_3$$

wherein the R groups are as defined above, in the presence of a base catalyst. It is preferred to use an amine, e.g., ammonia, primary, secondary or tertiary amines as catalyst since they appear to accelerate the reaction relative to other bases. The comments given above on method A as regards solvents, order of addition and ratio of reactants, temperature and product recovery also apply to this method. This method is not as generally applicable as is method A because of the non-availability of a wide variety of β-ketoamides.

These methods produce both the 6- and 7-isomers of those compounds wherein X is other than hydrogen because of the existence of a dynamic, tautomeric equilibrium in the X-substituted benzofuroxan. The isomers, actually a mixture of isomers, are recovered by methods known to those skilled in the art. In many of the preparations disclosed herein a solid, often crystalline material, separates from the reaction mixture. The solid appears to consist predominantly of one of the isomers, which isomer can be purified by repeated recrystallization from a suitable solvent to a constant melting point. The other isomer, the one present in smaller amounts in the solid material, is the predominant product in the mother liquor. It can be recovered therefrom by methods known to those skilled in the art, as, for example, by evaporation of the mother liquor and repeated crystallization of the residue to a product of constant melting point. Alternatively, the reaction mixture can be extracted with a suitable solvent, either before or after evaporation to dryness, and the extracted material which contains both isomers purified further by recrystallization. The separation and identification of some 6- and 7- isomers have been completed. Both isomers of a given compound, however, exhibit the same type of activity, e.g., as animal growth promotants or as antibacterial agents, to a significant degree.

Still another method (method C) involves the reaction of an ester of an appropriate 2-quinoxalinecarboxylic acid-1,4-di-oxide, e.g., the ethyl ester, with the appropriate amino containing reactant, such as those indicated under method A above in a suitable solvent. The reaction is conducted by mixing the ester with the amine reactant in a solvent such as acetonitrile, water or methanol at a temperature of from about 20°C. to about the reflux temperature of the solvent for a period of from about one hour to several days. The reaction period is, of course, dependent upon the temperature for a given system. The reactants are mixed preferably in a 1:1 molar ratio although excesses of either reactant can be used. The products are isolated as described above for method A.

Alternatively in accordance with method D, the benzofuroxan reactant can be allowed to react with an aceto ester, e.g., ethyl acetoacetate or ethyl pyruvate, with the appropriate amino containing reactant, such as those indicated under method A above, in a suitable solvent. The reaction is conducted in a similar manner to method C above.

Compounds wherein X is

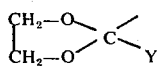

are prepared from the formyl or acetyl derivatives by reaction with ethylene glycol, usually an excess of ethylene glycol, in an organic solvent in the presence of an acid catalyst such as p-toluenesulfonic acid, methane or ethane sulfonic acid, hydrogen chloride or zince chloride. The preferred embodiment comprises refluxing a mixture of the appropriate formyl or acetyl benzofuroxan derivative with excess ethylene glycol, in the presence of p-toluenesulfonic acid (from about 2–10 mole percent based on the benzofuroxan reactant) in a solvent which permits azeotropic removal of water. Suitable solvents are benzene and toluene.

Such compounds, in addition to being antibacterial agents, are useful intermediates for preparation of compounds of this invention. Conversion of the formyl or acetyl group of the starting benzofuroxan reactant to the corresponding ethylene acetal or ketal affords better yields of the final 2-quinoxalinecarboxamide-1,4-dioxides than does direct reaction of the formyl or acetyl benzofuroxan in the herin described processes.

The 2-(1,3-dioxolanyl) and 2-(2-methyl-1,3-dioxolanyl) groups are subsequently converted back to formyl or acetyl by hydrolysis. The usual procedure comprises hydrolysis by means of an acid such as hydrochloric, sulfuric or perchloric acids in a solvent such as acetone at the reflux temperature. A variety of solvents can be used including benzene, toluene, methanol, methyl ethyl ketone. The temperature is not critical. However, the reaction is generally conducted at a temperature above 50°C. to accelerate reaction.

Preparation of the necessary benzofuroxan starting materials is illustrated in actual examples presented hereinafter. The other necessary reactants are either readily available or easily prepared by conventional synthetic means.

Acid addition salts of the compounds of the present invention which contain an ω-aminoalkyl group are prepared by methods well known to those skilled in the art. A convenient method comprises dissolving the free base in a suitable solvent, e.g., acetone, water, a lower alkanol such as ethanol or isopropanol, containing the desired acid or to which the desired acid is subsequently added. The salts are recovered by filtration, precipitation with a non-solvent, by evaporation of the solvent or, in the case of aqueous solutions, by lyophilization. In this manner, the hydrochloride, sulfate, nitrate, phosphate, acetate propionate, butyrate, citrate, gluconate, benzoate, pamoate, amsonate, tartrate, 3-hydroxy-2-naphthoate, the sulfosalicylate and other salts can be prepared.

The products of this invention are remarkedly effective in treating a wide variety of pathogenic microorganisms and are, therefore, useful as industrial antimicrobials, for example, in water treatment, slime-control, paint preservation and wood preservation as well as for topical application purposes as disinfectants.

For in vitro use, e.g., for topical application, it will often be convenient to compound the selected product with a pharmaceutically-acceptable carrier such as vegetable or mineral oil or an emollient cream. Similarly, they may be dissolved or dispersed in liquid carriers or solvents, such as water, alcohol, glycols or mixtures thereof or other pharmaceutically-acceptable inert media, that is, media which have no harmful effect on the active ingredient. For such purposes, it will generally be acceptable to employ concentrations of active ingredients of from about 0.01 percent to about 10 percent by weight based on total composition.

The compounds described herein, in contrast to the usual gram-negative activity of quinoxaline-1,4-dioxides, exhibit broad spectrum activity, that is, activity against both gram-negative and gram-positive bacteria, such as *Staphylococcus aureus*, *Streptomyces pyogenes*, *Escherichia coli* and *Pasturella multocida*.

When used in vivo for such purposes, these novel compounds can be administered orally or parenterally, e.g., by subcutaneous or intramuscular injection, at a dosage of from about 1 mg/kg to about 100 mg/kg of body weight. Vehicles suitable for parenteral injection may be either aqueous such as water, isotonic saline, isotonic dextrose, Ringer's solution, or nonaqueous such as fatty oils of vegetable origin (cotton seed, peanut oil, corn, sesame), dimethylsulfoxide and other non-aqueous vehicles which will not interfere with therapeutic efficiency of the preparation and are nontoxic in the volume or proportion used (glycerol, propylene glycol, sorbitol). Additionally, compositions suitable for extemporaneous preparation of solutions prior to administration may advantageously be made. Such compositions may include liquid diluents, for example, propylene glcyol, diethyl carbonate, glycerol, sorbitol, etc.; buffering agents, hyaluronidase, local anesthetics and inorganic salts to afford desirable pharmacological properties. These compounds may also be combined with various pharmaceutically-acceptable inert carriers including solid diluents, aqueous vehicles, non-toxic organic solvents in the form of capsules, tablets, lozenges, troches, dry mixes, suspensions, solutions, elixirs and parenteral solutions or suspensions. In general, the compounds are used in various dosage forms at concentration levels ranging from about 0.5 percent to about 90 percent by weight of the total composition. Other methods include mixing with animal feeds, the preparation of feed concentrates and supplements and dilute solutions or suspensions, e.g., a 0.1 percent solution, for drinking purposes.

The addition of a low level of one or more of the herein described substituted quinoxaline-2-carboxamide-1,4-dioxides to the diet of healthy animals, both ruminant and non-ruminant, such that these animals receive the product over an extended period of time, at a level of from about 1 mg/kg to about 100 mg/kg of body weight per day, especially over a major portion of their active growth period, results in an acceleration of the rate of growth and improves feed efficiency (the number of pounds of feed required to produce a pound gain in weight). Included in these two classes of animals are poultry (chickens, ducks, turkeys), cattle, sheep, dogs, cats, swine, rats, mice, horses, goats, mules, rabbits, mink, etc. The beneficial effects in growth rate and feed efficiency are over and above what is normally obtained with complete nutritious diets containing all the nutrients, vitamins, minerals, and other factors known to be required for the maximum healthy growth of such animals. The animals thus attain market size sooner and on less feed.

The feed compositions described are particularly valuable in the case of swine. In some instances the degree of response may vary with respect to the sex of the animals. The products may, of course, be administered in one component of the feed or they may be blended uniformly throughout a mixed fee; alternatively as noted above, they may be administered in an equivalent amount via the animal's water ration. It should be noted that a variety of feed components may be of use in the nutritionally balanced feeds. Any animal feed composition may be prepared to comprise the usual nutritional balance of energy, proteins, minerals and vitamins together with one or more of the quinoxaline-1,4-di-oxides described above. Some of the various components are commonly grains such as ground grain and grain by-products; animal protein substances, such as meat and fish by-products; vitaminaceous mixtures, e.g., vitamin A and D mixtures, riboflavin supplements and other vitamin B complexes; and bone meal, limestone and other inorganic compounds to provide minerals.

The relative proportions of the present compounds in feeds and feed concentrates may vary somewhat, depending upon the compound, the feed with which they are employed and the animal consuming the same. These substances are advantageously combined in such relative proportions with edible carriers as to provide pre-mixes or concentrates which may readily be blended with standard nutritionally balanced feeds or which may be used themselves as an adjunct to normal feedings.

In the preparation of concentrates a wide variety of carriers such as soybean oil meal, corn gluten meal, cotton seed oil meal, sunflower seed meal, linseed oil meal, cornmeal, limestone and corncob meal can be employed to facilitate uniform distribution of the active materials in the finished feed with which the concentrate is blended. The concentrate may be surface coated, if desired, with various proteinaceous materials of edible waxes, such as zein, gelatin, microcrystalline wax and the like to provide a protective film which seals in the active ingredients. The proportions of the drug preparation in such concentrates are capable of wide variation since the amount of active materials in the finished feed may be adjusted by blending the appropriate proportion of concentrate with the feed to obtain the desired degree of supplementation. In the preparation of high potency concentrates, i.e., pre-mixes, suitable for blending by feed manufacturers to produce finished feeds or concentrates of lower potency, the drug content may range from about 0.1 g to 50 g per pound of concentrate. The high potency concentrates may be blended by the feed manufacturer with proteinaceous carriers, such as soybean oil meal, to produce concentrated supplements which are suitable for direct feeding to animals. The proportion of the drug in these supplements may vary from about 0.1 to 10 g per pound of supplement. A particularly useful concentrate is provided by blending 2 g of drug with 1 pound of limestone or 1 pound of limestone-soybean oil meat (1:1). Other dietary supplements, such as vitamins, minerals, etc. may be added to the concentrates in the appropriate circumstances.

The concentrates described may also be added to animal feeds to produce a nutritionally balanced, finished feed containing from about 5 to about 125 g of the herein described compounds per ton of finished feed. In the case of ruminants, the finished feed should contain protein, fat, fiber, carbohydrate, vitamins and minerals, each in an amount sufficient to meet the nutritional requirements of the animal for which the feed is intended. Most of these substances are present in naturally occurring feed materials, such as alfalfa, hay or meal, cracked corn, whole oats, soybean oil meal, corn silage, ground corn cobs, wheat bran and dried molasses. Bone meal, limestone, iodized salt and trace minerals are frequently added to supply the necessary minerals and urea to provide additional nitrogen.

As is well-known to those skilled in the art, the types of diets are extremely variable depending upon the purpose, type of feeding operation, species, etc. Specific diets for various purposes are listed by Morrison in the Appendix of "Feeds and Feeding", the Morrison Publishing Company, Clinton, Iowa, 1959. In the case of non-ruminant animals, such as hogs, a suitable feed may contain from about 50 to 80 percent of grains, 3 to 10 percent animal protein, 5 to 30 percent vegetable protein, 2 to 4 percent of minerals, together with supplementary vitaminaceous sources.

The in vitro antibacterial activity of the quinoxaline-1,4-dioxides of the instant invention is demonstrated by the conventional two-fold serial dilution technique in Brain-Heart Infusion Broth (Difco). The broth is inoculated with bacteria and with the test quinoxaline-1,4-dioxide and then it is incubated overnight under anerobic conditions. On the next day, the test is read visually. The minimum inhibitory concentration (MIC) of the test compound is the lowest concentration which prevents turbidity, i.e., which prevents growth of the microorganism.

In determining in vivo activity of the quinoxaline-1,4-dioxides of this invention, the test compound is administered to mice which have been infected by intra-parenteral injection of a lethal inoculum of pathogenic bacteria. The test compound is administered using a multiple dosing regimen and using either the oral (PO) or the subcutaneous (SC) route. The inoculum of bacteria varies from about 1 to about 10 times the amount needed to kill 100% of the mice under the conditions of the test. At the end of the test, the activity of the compound is assessed by counting the number of survivors among the treated animals.

In vitro and in vivo activity of representative compounds of this invention, determined as aforesaid, are reported in the following tabulation for compounds of the formula:

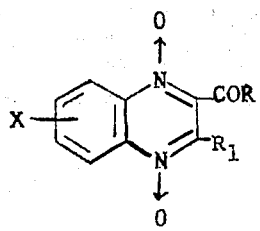

The following examples illustrate the preparation of representative compounds of the present invention. The alphabetic method designations therein correspond to the counterpart designations heretofore presented.

EXAMPLE 1

The following illustrates method A having the equation:

| R | X | $R_1$ | IN VITRO MIC (mcg./ml.) Strep. pyogenes | E. coli | IN VIVO Survivors-SC[a](PO)[b] 50 mg./kg. Strep. pyogenes | 25 mg./kg. E. coli |
|---|---|---|---|---|---|---|
| $NH_2$ | 6-$COCH_3$ | $CH_3$ | <0.391 | <0.391 | 10/10(9/10) | 5/5(5/5) |
| $NH_2$ | 7-$COCH_3$ | $CH_3$ | 0.391 | <0.391 | 5/5 (4/5) | 5/5 |
| $NH_2$ | 6(7)-$COCH_3$ | $CH_3$ | 0.195 | 0.195 | 8/10 | 8/10 |
| $NHCH_3$ | 6-$COCH_3$ | $CH_3$ | 0.781 | <0.391 | 3/5(2/5) | 8/10(7/10) |
| $NHCH_3$ | 7-$COCH_3$ | $CH_3$ | 0.391 | 0.391 | 5/10(9/10) | 6/10 |
| $N(CH_3)_2$ | 6-$COCH_3$ | $CH_3$ | 6.25 | 6.25 | 6/10(5/10)[c] | 1/5(0/5) |
| $N(CH_3)_2$ | 7-$COCH_3$ | $CH_3$ | 6.25 | 6.25 | 6/10(2/10) | 0/10 |
| $NHCH_2CH_2OH$ | 6-$COCH_3$ | $CH_3$ | <0.391 | <0.391 | 5/10(2/10) | 3/10(c) |
| $NHCH_2CH_2OH$ | 6(7)-$COCH_3$ | $CH_3$ | 1.562 | 25 | 8/10(1/10) | 3/10 |
| $NHCH_3$ | 6(7)-$COCH_3$ | H | <0.391 | 1.562 | 10/10(8/10) | 0/10 |
| $NH_2$ | 7-O-C($CH_3$)-O | $CH_3$ | 12.5 | 12.5 | 4/5(4/5) | 5/5(3/5) |
| $NH_2$ | 6(7)- " | $CH_3$ | 6.25 | 3.125 | 8/10(8/10) | 5/10 |
| $NHCH_3$ | 6(7)- " | $CH_3$ | <0.391 | 12.5 | 4/10(4/10) | 8/10 |
| $N(CH_3)_2$ | 6(7)- " | $CH_3$ | 25 | 100 | 7/10(8/10) | 1/10 |
| $NHCH_2CH_2OH$ | 6(7)- " | $CH_3$ | 25 | 50 | 0/10(0/10) | 4/10 |
| $NHCH_2CH_2N(CH_3)_2$ | 6(7)- " | $CH_3$ | 6.25 | 100 | 6/10(3/10) | 0/10 |
| $NH_2$ | 6(7)- " | H | 3.125 | <0.391 | 7/10(8/10) | 0/10 |
| $NHCH_3$ | 6(7)- " | H | <0.391 | 25 | 9/10(9/10) | 6/10 |
| $NH_2$ | 6(7)-CH(OH)$CH_3$ | $CH_3$ | 100 | 25 | 2/10(4/10) | 9/10 |
| $NHCH_3$ | 6(7)-CH(OH)$CH_3$ | $CH_3$ | 100 | 25 | 10/10(9/10) | 5/10 |
| $N(CH_3)_2$ | 6(7)-CH(OH)$CH_3$ | $CH_3$ | 50 | 50 | 3/10(3/10) | 7/10 |
| $NHCH_2CH_2OH$ | 6(7)-CH(OH)$CH_3$ | $CH_3$ | >200 | 100 | 1/10(1/10) | 3/9 |
| $NHCH_2CH_2N(CH_3)_2$ | 6(7)-CH(OH)$CH_3$ | $CH_3$ | 25 | 100 | 4/10(0/10) | 2/10 |
| N⟨ ⟩N—$CH_3$ · HCl | 6(7)-CH(OH)$CH_3$ | $CH_3$ | 25 | 200 | 1/10(1/10) | 4/10 |
| $NH_2$ | 6(7)-CHO | $CH_3$ | 3.125 | 1.562 | 2/10(1/10) | 3/10 |
| $NHCH_3$ | 6(7)-CHO | $CH_3$ | 1.562 | 3.125 | 0/10(0/10) | 3/10 |
| $N(CH_3)_2$ | 6(7)-CHO | $CH_3$ | 6.25 | 12.5 | 0/10(0/10) | 2/10 |
| $NHCH_2CH_2OH$ | 6(7)-CHO | $CH_3$ | 25 | 25 | 5/10(2/10) | 3/10 |
| $NH_2$ | 6(7)-O-CH-O | $CH_3$ | 6.25 | 6.25 | 7/10(3/10) | 6/10 |
| $NHCH_3$ | 6(7)- " | $CH_3$ | 0.781 | 6.25 | 4/10(5/10) | 2/10 |
| $N(CH_3)_2$ | 6(7)- " | $CH_3$ | 6.25 | 50 | 0/10(0/10) | 0/10 |
| $NHCH_2CH_2OH$ | 6(7)- " | $CH_3$ | 0.781 | 25 | 2/10(3/10) | 3/10 |
| $NHCH_2CH_2N(CH_3)_2$ | 6(7)- " | $CH_3$ | 12.5 | 50 | 10/10(8/10) | 0/10 |
| N⟨ ⟩N—$CH_3$ | 6(7)- " | $CH_3$ | 3.125 | 25 | 1/10(1/10) | 0/10 |
| $NH_2$ | 6(7)-$CH_2OH$ | $CH_3$ | 25 | 25 | 2/10(3/10) | 10/10 |
| $NHCH_3$ | 6(7)-$CH_2OH$ | $CH_3$ | 50 | 25 | 3/10(3/10) | 8/10 |
| $NHCH_3$ | 7-$CH_2OH$ | $CH_3$ | >200 | 6.25 | 2/10(1/10) | 9/10 |
| $N(CH_3)_2$ | 6(7)-$CH_2OH$ | $CH_3$ | 50 | 50 | 3/10(1/10) | 6/10 |
| $NHCH_2CH_2OH$ | 6(7)-$CH_2OH$ | $CH_3$ | >200 | 100 | 3/10(1/10) | 3/10 |
| $OCH_2CH_3$ | 6(7)-$CH_2OH$ | $CH_3$ | 25 | 25 | 6/10(5/10) | 4/10 |
| $NHCH_2CH_2N(CH_3)_2$ | 6(7)-$CH_2OH$ | $CH_3$ | 25 | 100 | 3/10(1/10) | 2/10 |
| N⟨ ⟩N—$CH_3$ · HCl | 6(7)-$CH_2OH$ | $CH_3$ | 12.5 | 50 | 0/10(2/10) | 3/10 |
| $NH_2$ | 6(7)-$CH_2OH$ | H | 6.25 | <0.391 | 10/10(4/10) | 7/10 |
| $NHCH_3$ | 6(7)-$CH_2OH$ | H | 0.781 | 1.562 | 10/10(6/10) | 4/10 |
| $NHCH_2CH_2OH$ | 6(7)-$CH_2OH$ | H | 25 | 25 | | |
| $NHCH_2CH_2N(CH_3)_2$ | 6(7)-$CH_2OH$ | H | <0.391 | 6.25 | 10/10(10/10) | 0/10 |

[a]SC = subcutaneous
[b](PO) = data in parenthesis based on oral administration
[c]dosage = 100 mg./kg.

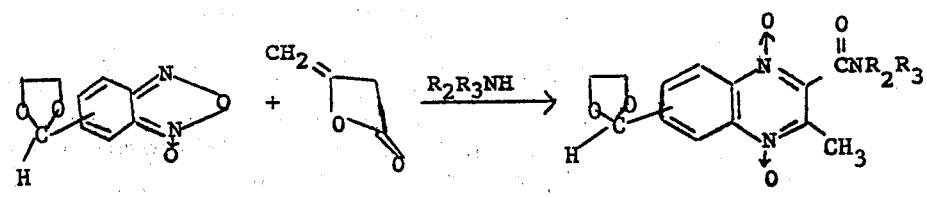

6-(7)-Formyl-N-(2-Hydroxyethyl)-3-Methyl-2-Quinoxalinecarboxamide 1,4-Dioxide Ethylene Acetal A solution of 2-hydroxyethylamine (0.92g, 0.015 mole) in tetrahydrofuran (4 ml) was added to a stirred solution of diketene (1.32g, 0.015 mole) in tetrahydrofuran (7 ml) at a temperature of 0°C. 5(6)-Formylbenzofuroxan, ethylene acetal (3.12g, 0.015 mole) in a tetrahydrofuran (7 ml) is added to the reaction mixture with good stirring. The mixture was allowed to stand at room temperature overnight and the product filtered off. Recrystallization from methanol yielded 3.25g (64%): mp 199°–200°C.

EXAMPLE 2

The following illustrates method B having the equation:

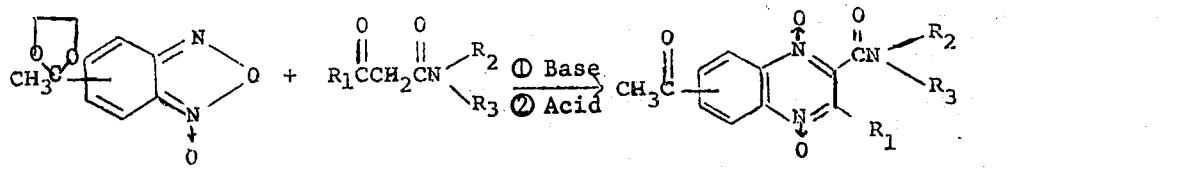

6- and 7-Acetyl-3-Methyl-2-Quinoxalinecarboxamide 1,4-dioxide

5(6)-Acetylbenzofuroxan ethylene ketal (6.66 g., 0.03 mole) and acetoacetamide (3.03 g., 0.03 mole) were dissolved in 25 ml. of tetrahydrofuran. Methylamine in water (1 ml. 40% solution) was added and the reaction mixture was stirred at room temperature 3 days. The pale yellow solid was collected by suction filtration and washed thoroughly with tetrahydrofuran: 7.68 g (84%); m.p. 207°–209°c; ca. 50:50 mixture of 6- and 7-isomers based on spectral data.

The ethylene ketal produced in this manner (27 g., 0.089 mole) was dissolved in 2.5 l of acetone and 150 ml. of 1 N hydrochloric acid, and the solution was refluxed for 5 hours. During this time yellow crystals precipitated that were collected by suction filtration upon terminating the reaction. The crystals were washed thoroughly with acetone: 11.5 g (50%); m.p. 229°–230°C; 7-isomer based on spectral data (less than 10% of the 6-isomer was present). The mother liquor was concentrated under vacuum causing additional material to precipitate; 10.4 g (45%); m.p. 216°–217°C; 6-isomer based on spectral data (less than 10% of the 7-isomer was present). The combined yield of 6- and 7-isomers was 95% of the theoretical.

EXAMPLE 3

The following illustrates method C having the equation:

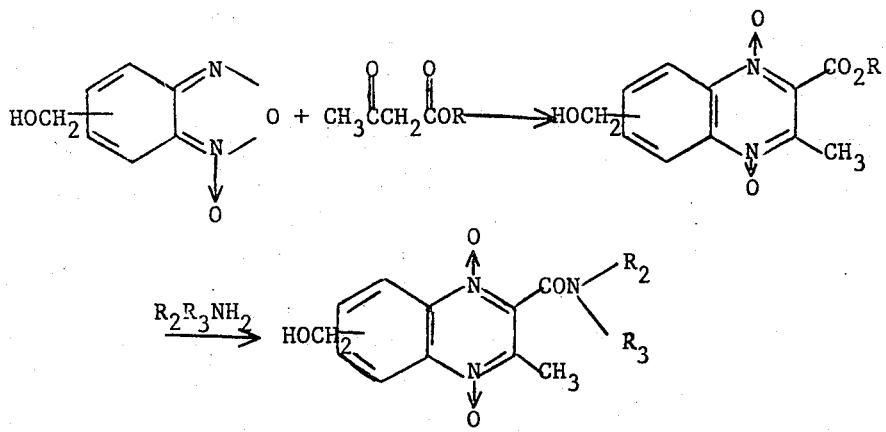

Ethyl 6(7)-Hydroxymethyl-3-Methyl-2-Quinoxaline-Carboxylate 1,4-Dioxide

5(6)-Hydroxymethylbenzofuroxan (2.00 g., 0.013 mole) and ethyl acetoacetate (2.24 g. 0.017 mole) were dissolved in 2-propanol (50 ml) and the mixture was maintained at 60°C. Calcium hydroxide (0.097 g., 0.0013 mole) was added in small portions and the reaction mixture was kept at 60°C for several hours. The mixture was cooled to room temperature and the solvent was removed under vacuum. The residue was taken up in chloroform and then methanol was added causing product to crystallize: 1.64 g (45% yield); m.p. 188°–190°C.

N,3-Dimethyl-6(7)-Hydroxymethyl-2-Quinoxalinecarboxamide 1,4-Dioxide

Ethyl 6(7)-hydroxymethyl-3-methyl-2-quinoxalinecarboxylate 1,5-dioxide (1.00g., 0.0036 mole) was added to 40% aqueous methylamine solution (10 ml). The slurry was warmed on a steam bath to achieve solution and then allowed to cool to room temperature. The product was filtered off and recrystallized from methanol.

EXAMPLE 4

The following illustrates method D having the equation:

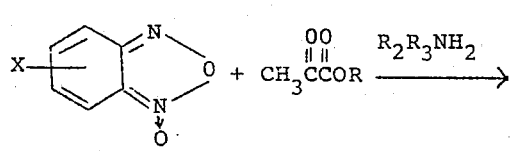 + 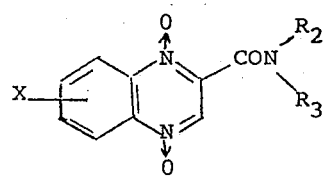

N-Methyl-6(7)-Hydroxymethyl-2-Quinoxalinecarboxamide 1,4-Dioxide

5(6)-Hydroxymethylbenzofuroxan (3.32g., 0.02 mole) and ethyl pyruvate (5.30g., 0.02 mole) were dissolved in acetonitrile (40 ml) and methylamine gas was bubbled into the reaction mixture for 8 minutes. Within a few hours solid precipitated and the product was filtered off to afford 2.3g (45% yield): mp 209°–211°C.

EXAMPLE 5

Compounds of the following formula were prepared by one of the foregoing methods:

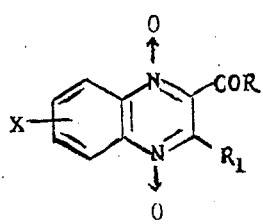

| R | X | $R_1$ | Melting Point °C. |
|---|---|---|---|
| $NH_2$ | 6-$COCH_3$ | $CH_3$ | 216–217 |
| $NH_2$ | 7-$COCH_3$ | $CH_3$ | 229–230 |
| $NH_2$ | 6(7)-$COCH_3$ | $CH_3$ | 217–220 |
| $NHCH_3$ | 6-$COCH_3$ | $CH_3$ | 208–209 |
| $NHCH_3$ | 7-$COCH_3$ | $CH_3$ | 196–198 |
| $N(CH_3)_2$ | 6-$COCH_3$ | $CH_3$ | 192–194 |
| $N(CH_3)_2$ | 7-$COCH_3$ | $CH_3$ | 188–190 |
| $NHCH_2CH_2OH$ | 6-$COCH_3$ | $CH_3$ | 183–184 |
| $NHCH_2CH_2OH$ | 6(7)-$COCH_3$ | $CH_3$ | 190–192 |
| $NHCH_3$ | 6(7)-$COCH_3$ | H | 248–249 |
| $NH_2$ | 7-O\C(CH_3)/O | $CH_3$ | 214–215 |
| $NH_2$ | 6(7)- " | $CH_3$ | 207–209 |
| $NHCH_3$ | 6(7)- " | $CH_3$ | 196–197 |
| $N(CH_3)_2$ | 6(7)- " | $CH_3$ | 113–116 |
| $NHCH_2CH_2OH$ | 6(7)- " | $CH_3$ | 100–105 |
| $NHCH_2CH_2N(CH_3)_2$ | 6(7)- " | $CH_3$ | 76–85 |
| $NH_2$ | 6(7)- " | H | 205–206 |
| $NHCH_3$ | 6(7)- " | H | 241–244 |
| $NH_2$ | 6(7)-CH(OH)$CH_3$ | $CH_3$ | 220–221 |
| $NHCH_3$ | 6(7)-CH(OH)$CH_3$ | $CH_3$ | 202–204 |
| $N(CH_3)_2$ | 6(7)-CH(OH)$CH_3$ | $CH_3$ | 208–211 |
| $NHCH_2CH_2OH$ | 6(7)-CH(OH)$CH_3$ | $CH_3$ | 87–90 |
| $NHCH_2CH_2N(CH_3)_2$ | 6(7)-CH(OH)$CH_3$ | $CH_3$ | 68–72 |
| N⌐N—$CH_3$ · HCl | 6(7)-CH(OH)$CH_3$ | $CH_3$ | 214–215 |
| $NH_2$ | 6(7)-CHO | $CH_3$ | 233–234 |
| $NHCH_3$ | 6(7)-CHO | $CH_3$ | 216–218 |
| $N(CH_3)_2$ | 6(7)-CHO | $CH_3$ | 195–197 |
| $NHCH_2CH_2OH$ | 6(7)-CHO | $CH_3$ | 236–237 |
| $NH_2$ | 6(7)-C(O)(O)CH | $CH_3$ | 177–179 |
| $NHCH_3$ | 6(7)-" | $CH_3$ | 196–198 |
| $N(CH_3)_2$ | 6(7)-" | $CH_3$ | 184–187 |
| $NHCH_2CH_2OH$ | 6(7)-" | $CH_3$ | 199–200 |
| $NHCH_2CH_2N(CH_3)_2$ | 6(7)-" | $CH_3$ | 76–85 |
| N⌐N—$CH_3$ | 6(7)-" | $CH_3$ | 175–178 |
| $NH_2$ | 6(7)-$CH_2OH$ | $CH_3$ | 225–226 |
| $NHCH_3$ | 6(7)-$CH_2OH$ | $CH_3$ | 173–176 |
| $NHCH_3$ | 7-$CH_2OH$ | $CH_3$ | 199–201 |
| $N(CH_3)_2$ | 6(7)-$CH_2OH$ | $CH_3$ | 218–219 |
| $NHCH_2CH_2OH$ | 6(7)-$CH_2OH$ | $CH_3$ | 195–198 |
| $NHCH_2CH_2N(CH_3)_2$ | 6(7)-$CH_2OH$ | $CH_3$ | 162–164 |
| N⌐N—$CH_3$ | 6(7)-$CH_2OH$ | $CH_3$ | 210–213 |
| $NH_2$ | 6(7)-$CH_2OH$ | H | 215–216 |
| $NHCH_3$ | 6(7)-$CH_2OH$ | H | 209–211 |
| $NHCH_2CH_2OH$ | 6(7)-$CH_2OH$ | H | 176–178 |
| $NHCH_2CH_2N(CH_3)_2$ | 6(7)-$CH_2OH$ | H | 183–184 |

EXAMPLE 6

The compounds indicated below are prepared by the appropriate previously described and illustrated method:

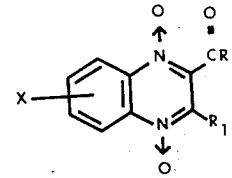

| 6(7)-X | $R_1$ | R |
|---|---|---|
| CHO | H | $NHC_2H_5$ |
| $CH_2OH$ | $CH_3$ | $NHn-C_4H_9$ |
| $COCH_3$ | $CH_3$ | $N(n-C_4H_9)_2$ |
| $COCH_3$ | H | $N(t-C_4H_9)_2$ |
| $CH(OH)CH_3$ | H | $N(CH_2)_3OH$ |
| $CH_2OH$ | $CH_3$ | $N(CH_2)_2OCH_3$ |
| $CH_2$—O\C/\$CH_3$ $CH_2$—O/ | H | $N(CH_2)_3OCH_3$ |
| $CH_2OH$ | H | $(CH_2)_2NH_2$ |
| $COCH_3$ | $CH_3$ | $(CH_2)_3NH_2$ |
| $COCH_3$ | $CH_3$ | $(CH_2)_2NH(CH_3)$ |
| $CH(OH)CH_3$ | H | $(CH_2)_3NH(CH_3)$ |
| CHO | $CH_3$ | $(CH_2)_3N(CH_3)_2$ |
| $CH_2OH$ | H | $(CH_2)_2N(CH_3)_2$ |
| $COCH_3$ | $CH_3$ | —NCH=CHCH=CH |
| $CH(OH)CH_3$ | $CH_3$ | —NCH$_2$CH$_2$CH$_2$ |
| CHO | H | —NCH$_2$CH$_2$CH$_2$CH$_2$ |
| CHO | H | —NCH$_2$CH$_2$OCH$_2$CH$_2$ |
| $CH_2$—O\C/\H $CH_2$—O/ | $CH_3$ | —NCH$_2$CH$_2$SCH$_2$CH$_2$ |
| $CH_2OH$ | H | —NCH$_2$CH$_2$NHCH$_2$CH$_2$ |
| $COCH_3$ | H | —NCH$_2$CH$_2$N(CH$_3$)CH$_2$CH$_2$ |

-continued
EXAMPLE 6
The compounds indicated below are prepared by the appropriate previously described and illustrated method:

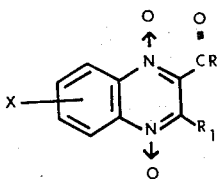

| 6(7)-X | R₁ | R |
|---|---|---|
| CH(OH)CH₃ | CH₃ | —NCH₂CH₂N(t.C₄H₉)CH₂CH₂ |
| COCH₃ | CH₃ | —NCH₂CH₂N(CH₂CH₂OH)CH₂CH₂ |
| CH₂OH | CH₃ | —NCH₂CH₂N(n-C₄H₈OH)CH₂CH₂ |
| CHO | H | —NCH₂CH₂N(COC₃H₇)CH₂CH₂ |
| CH₂—O \\ C / CH₂—O | CH₃ CH₃ | —NCH₂CH₂N(COOC₄H₉)CH₂CH₂ |
| CH₂OH | H | —NCH₂CH₂N(COOCH₃)CH₂CH₂ |

The following examples illustrate the preparation of typical benzofuroxan starting materials used in the preceding examples.

EXAMPLE 7
5(6)-Acetylbenzofuroxan a. Diazonium Salt Method

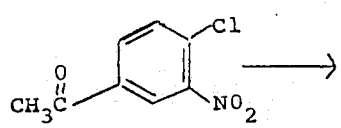

A mixture of 45.5 g (0.25 mole) of 3-nitro-4-aminoacetophenone, 80 ml of ice-water, 375 ml of acetic acid, and 190 ml of concentrated sulfuric acid is placed in a 2-l three-necked flask equipped with a stirrer, a thermometer, and a dropping funnel. The stirrer is started, and the flask is cooled in ice-methanol bath until the temperature of the mixture is 0°–5°C. After this temperature has been reached, the amine hydrochloride is diazotized by adding dropwise a solution of 38 g sodium nitrite in 75 ml of water. Stirring is then continued for one-half hour at 0°–5°C. Urea (38 g) in 75 ml of water is added to destroy the excess nitrous acid. With stirring, a solution of 17.3g (0.25 mole) of sodium azide in 75 ml of water is added. Almost immediately, a light yellow precipitate is formed, which is collected on a Büchner funnel after the nitrogen evolution has ceased (20–30 minutes). This crude product of phenylazide is added to 100 ml of toluene in a 500-ml round-bottomed flask equipped with a reflux condenser and a Dean-Stark trap. The mixture is refluxed for 3 hours until there are no more visible signs of gas evolution. The solution is cooled in an ice-bath, and after a few minutes a light yellow solid precipitates. The solid is collected on a sintered-glass funnel 23.1 g; m.p. 90°–91°C. Evaporation of the toluene mother liquor yields another 20 g of the oxide, m.p. 84°–86°C, which may be purified by recrystallization from methanol to give material having a melting point of 90°–91°C. The total yield is 39.2 g (88%).

b. Chloride Displacement Method

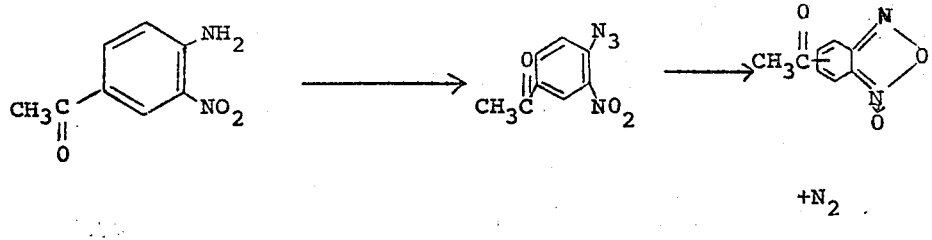

A mixture of 4-chloro-3-nitroacetophenone (112 g, 0.56 mole) and sodium azide (36.5 g, 0.56 mole) in 675 ml of dimethylsulfoxide was stirred overnight at room temperature. The reaction mixture was poured into 2 l. of water and the solution was extracted with seven 300-ml portions of toluene. The toluene extract was dried over anhydrous magnesium sulfate and then heated under reflux until nitrogen evolution had ceased (ca. one hour). The solvent was removed under vacuum leaving a yellow solid: 74 g (74%); m.p. 89°–91°C.

EXAMPLE 8
5(6)-Acetyl-Benzofuroxan Ethylene Ketal

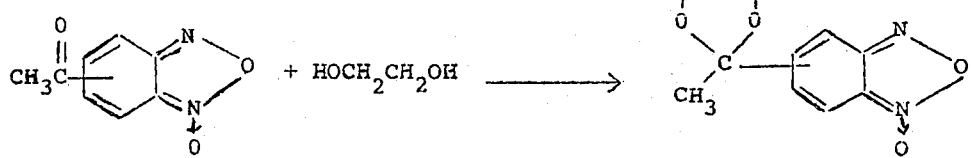

To 5(6)-acetyl-benzofuroxan (11.0 g, 0.062 mole) dissolved in 900 ml of toluene was added ethylene glycol (160 ml) and p-toluenesulfonic acid (0.7 g). The

EXAMPLE 11

5(6)-Hydroxymethyl-Benzofuroxan

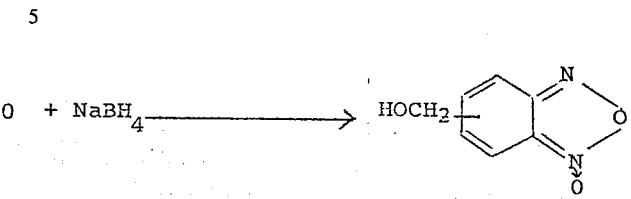

two-phase mixture was refluxed for 6 hours and water was removed during the course of the reaction by means of a Dean-Stark trap. The reaction mixture was then cooled to room temperature and the toluene layer was separated and washed four times with 300-ml portions of water, and dried over anhydrous magnesium sulfate. The toluene was removed in vacuo, and the resulting solid was recrystallized from ether-hexane: yellow crystals; 10.3 g (83%); m.p. 80°–81°C.

5(6)-Formyl-BFO (10.0 g, 0.061 mole) was dissolved in 500 ml of methanol. Sodium borohydride (0.73 g, 0.019 mole) was added in small portions over 10 minutes, causing the solution to turn red. The reaction mixture was stirred an additional 10 minutes and 70 ml of water was added. The methanol was removed in vacuo and the remaining aqueous solution was extracted with five 50-ml portions of chloroform. The combined chloroform extract was dried over anhydrous magnesium sulfate, and the solvent was removed in vacuo leaving a yellow liquid that crystallized upon cooling to 5°C. The product was recrystallized from ether-hexane: 9.0G (90%); pale yellow crystals; m.p. 58°–59°.

EXAMPLE 9

5(6)-(1-Hydroxyethyl)-Benzofuroxan

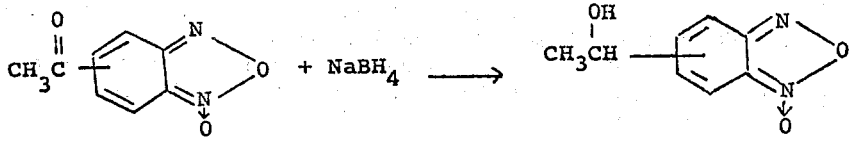

5(6)-Acetyl-benzofuraxon (10.0g, 0.056 mole) was dissolved in 450 ml of methanol. Sodium borohydride (0.63 g, 0.017 mole) was added in small portions over 10 minutes, causing the solution to turn red. The reaction mixture was stirred an additional 10 minutes and 70 ml of water was added. The methanol was removed in vacuo and the remaining aqueous solution was extracted with five 50-ml portions of chloroform. The combined chloroform extract was dried over anhydrous magnesium sulfate, and the solvent was removed in vacuo leaving a yellow-orange liquid: 8.9 g (89%).

EXAMPLE 10

5(6)-Formyl-Benzofuroxan Ethylene Ketal

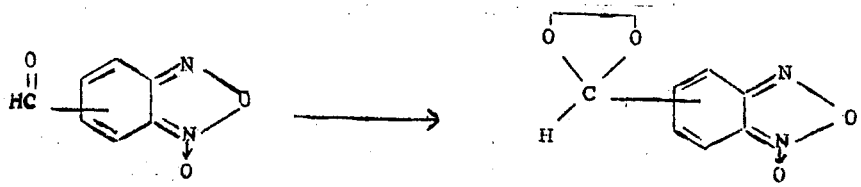

To 5(6)-formyl-benzofuroxan (21.0 g, 0.128 mole) dissolved in 1100 ml of toluene was added ethylene glycol (300 ml) and p-toluenesulfonic acid (1.4 g). The two-phase mixture was refluxed for 5 hours and water was removed during the course of the reaction by means of a Dean-Stark trap. The reaction mixture was then cooled to room temperature and the toluene layer was separated and washed three times with 100-ml portions of water, and dried over anhydrous magnesium sulfate. The toluene was removed in vacuo, and the resulting solid was recrystallized from ether-hexane: yellow crystals; 22.9 g (86%); m.p. 60°–62°C.

EXAMPLE 12

The acid addition salts of the compounds of the present invention which contain an ω-aminoalkyl moiety are prepared by dissolving the appropriate 3-substituted quinoxaline-2-carboxamide-1,4-dioxide (0.01 mol) in ethanol and then adding a stoichiometric amound of the selected acid. The resulting solution is stirred at room temperature for 30 minutes and the acid salt may be recovered by evaporation of the solvent or by precipitation with a non-solvent, e.g., ether. In this way, the acid addition salts of sulfuric, nitric, phosphoric, acetic, hydrochloride propionic, butyric, citric, gluconic, benzoic, pamoic, amsonic, tartaric, 3-hydroxy-2-naphthoic and sulfosalicylic acid are prepared.

What is claimed is:

1. A compound selected from the group consisting of

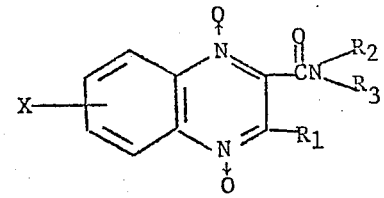

wherein X is a 6- or 7-position substituent selected from the group consisting of formyl, acetyl, hydroxymethyl, 1-hydroxyethyl and

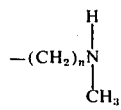

wherein Y is selected from the group consisting of hydrogen and methyl; $R_1$ is hydrogen or methyl; $R_2$, when taken separately, is hydrogen or alkyl having 1 to 4 carbon atoms; $R_3$, when taken separately, is hydrogen, alkyl having 1 to 4 carbon atoms, $-(CH_2)_nOH$, $-(CH_2)_nOCH_3$, $-(CH_2)_nNH_2$, $$-(CH_2)_n\underset{CH_3}{\overset{H}{N}}$$

or $$-(CH_2)_n\underset{CH_3}{\overset{CH_3}{N}}$$

wherein $n$ is 2 or 3 and $R_2$ and $R_3$, when taken together with the nitrogen atom to which they are attached, form a member selected from the group consisting of pyrrolo, pyrrolidino, piperidino, and the pharmaceutically acceptable acid addition salts of those compounds wherein $R_2$ has an ω-aminoalkyl moiety.

2. A compound according to claim 1 wherein X is acetyl; $R_1$ is methyl and each of $R_2$ and $R_3$ is hydrogen or methyl.

3. A compound according to claim 1 wherein X is hydroxy-methyl; $R_1$ is methyl and each of $R_2$ and $R_3$ is hydrogen or methyl.

4. A compound according to claim 1 wherein X is 1-hydroxy-ethyl; $R_1$ is methyl and each of $R_2$ and $R_3$ is hydrogen or methyl.

5. A compound according to claim 1 wherein X is

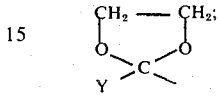

$R_1$ is methyl and each of $R_2$ and $R_3$ is hydrogen or methyl.

6. The compound according to claim 2 wherein each of $R_2$ and $R_3$ is hydrogen.

7. The compound according to claim 2 wherein $R_2$ is hydrogen and $R_3$ is methyl.

8. The compound according to claim 3 wherein each of $R_2$ and $R_3$ is hydrogen.

9. The compound according to claim 3 wherein $R_2$ is hydrogen and $R_3$ is methyl.

10. The compound according to claim 4 wherein each of $R_2$ and $R_3$ is methyl.

11. The compound according to claim 5 wherein Y is methyl and each of $R_2$ and $R_3$ is hydrogen.

* * * * *

UNITED STATES PATENT AND TRADEMARK OFFICE
CERTIFICATE OF CORRECTION

PATENT NO. : 3,948,911
DATED : April 6, 1976
INVENTOR(S) : James W. McFarland

It is certified that error appears in the above-identified patent and that said Letters Patent are hereby corrected as shown below:

Col. 1, lines 43-47, that portion of the formula reading

" $\begin{array}{c}CH-\\|\\CH_2-\end{array}$ " should read -- $\begin{array}{c}CH_2-\\|\\CH_2-\end{array}$ --.

Col. 2, line 50, "$HNR_2R$" should read -- $HNR_2R_3$ --.

Col. 15, Example 6, lines 21-22, under heading "6(7)-X"

" $\begin{array}{c}CH_2-O\\ \phantom{xx}\diagdown\\ \phantom{xxx}C\\ \phantom{xx}\diagup\phantom{xx}\\ CH_2-O\phantom{xx}CH_3\end{array}$ " should read --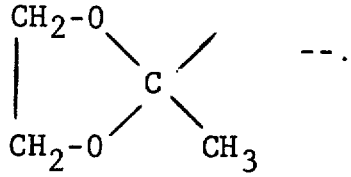--.

Signed and Sealed this

Twentieth Day of July 1976

[SEAL]

Attest:

RUTH C. MASON
*Attesting Officer*

C. MARSHALL DANN
*Commissioner of Patents and Trademarks*